(12) United States Patent
Caluser

(10) Patent No.: US 9,700,281 B2
(45) Date of Patent: *Jul. 11, 2017

(54) SENSOR ATTACHMENT FOR THREE DIMENSIONAL MAPPING DISPLAY SYSTEMS FOR DIAGNOSTIC ULTRASOUND MACHINES

(71) Applicant: Metritrack, Inc., Hillside, IL (US)

(72) Inventor: Calin Caluser, Glen Ellyn, IL (US)

(73) Assignee: Metritrack, Inc., Hillside, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/833,419

(22) Filed: Aug. 24, 2015

(65) Prior Publication Data

US 2015/0359513 A1   Dec. 17, 2015

Related U.S. Application Data

(63) Continuation of application No. 13/843,080, filed on Mar. 15, 2013, now Pat. No. 9,119,585.

(51) Int. Cl.
*A61B 8/00* (2006.01)
*A61B 8/14* (2006.01)
*A61B 8/08* (2006.01)

(52) U.S. Cl.
CPC ............ *A61B 8/4263* (2013.01); *A61B 8/085* (2013.01); *A61B 8/0825* (2013.01); *A61B 8/14* (2013.01); *A61B 8/4209* (2013.01); *A61B 8/4236* (2013.01); *A61B 8/4254* (2013.01); *A61B 8/44* (2013.01); *A61B 8/4416* (2013.01)

(58) Field of Classification Search
CPC ......... A61B 8/0825; A61B 8/085; A61B 8/14; A61B 8/4209; A61B 8/4236; A61B 8/4254; A61B 8/4263; A61B 8/44; A61B 8/4416

See application file for complete search history.

(56) References Cited

U.S. PATENT DOCUMENTS

| | | | |
|---|---|---|---|
| 9,119,585 B2 * | 9/2015 | Caluser | A61B 8/085 |
| 9,439,624 B2 * | 9/2016 | Caluser | A61B 5/06 |
| 2009/0124906 A1 | 5/2009 | Caluser | |
| 2009/0171236 A1 | 7/2009 | Davies | |
| 2014/0163376 A1 | 6/2014 | Caluser | |
| 2015/0051489 A1 * | 2/2015 | Caluser | A61B 8/0825 600/440 |
| 2015/0182191 A1 * | 7/2015 | Caluser | A61B 5/4312 600/440 |

FOREIGN PATENT DOCUMENTS

WO     03103500 A1   12/2003

* cited by examiner

*Primary Examiner* — Michael Rozanski
(74) *Attorney, Agent, or Firm* — Ziolkowski Patent Solutions Group, SC

(57) ABSTRACT

A sensor attachment for use with three dimensional ultrasound mapping devices is presented. According to the invention, one or more sensors are attached to specific locations on the body, such as the nipple and sternum, the inventive sensor attachments enabling accurate recording of target information, including location and size; the present invention especially helpful in subsequent and comparative examinations. A method of use is also presented.

19 Claims, 18 Drawing Sheets

SENSOR ATTACHMENT FOR THREE DIMENSIONAL MAPPING DISPLAY SYSTEMS FOR DIAGNOSTIC ULTRASOUND MACHINES

CROSS-REFERENCE TO RELATED APPLICATION

The present application is a continuation of and claims priority to U.S. application Ser. No. 13/843,080 filed Mar. 15, 2013, now U.S. Pat. No. 9,119,585, the disclosure of which is incorporated herein in its entirety.

I. TECHNICAL FIELD

The present invention relates to diagnostic ultrasound technology and, more particularly, to a sensor attachment apparatus for use in three dimensional mapping display ("TDMD") diagnostic ultrasound systems.

II. BACKGROUND OF THE INVENTION

Ultrasound is an important imaging modality for medical diagnostic purposes and as a guidance tool for diagnostic or therapeutic procedures, like soft tissue needle biopsy, tumor ablation, etc. Ultrasound can be used over the entire human body and has certain advantages over other modalities, including, among others: the ability to locate and characterize medical problems; lower cost compared to modalities such as MRI and CT; real time operation; and, the lack of ionizing radiation with the known associated health risks.

Ultrasound imaging systems transmit sound waves of very high-frequency (e.g., 1 MHz to 20 MHz) into the patient's body and the echoes scattered from structures in the patient's body are processed to create and display images and information related to these structures.

Ultrasound imaging can be applied to various regions or organs in the body. For example, a breast ultrasound procedure involves the placement of an ultrasound transducer over a region of interest of the breast with the radiologist or other medical professional (the "user") viewing a real-time ultrasound image output on a display. The ultrasound machine monitor usually displays relevant text and/or graphical information next to the ultrasound image for simultaneous viewing by the user. The user can freeze a displayed image with medical findings of interest, and the corresponding image can be printed on a primer or stored in digital format.

2D free hand ultrasound imaging, the most common technique used today, represents a slice through the region of interest. 3D ultrasound scanning is available; however, it is usually used in conjunction with 2D scanning techniques. Currently, most diagnostic studies are performed using 2D scanning technique.

The vast majority of ultrasound guided biopsies and other invasive ultrasound guided invasive procedures done by free hand and other more automated modes use the ultrasound machine 2D display mode. Therefore, it is desirable to have a fast and accurate way to find the target during such invasive procedures.

It is important to accurately store positional annotations for later evaluation, since this is essential for final interpretation, diagnosis, and treatment. As digital storage and communication of medical information replace hard copy based storage and communication technologies, the accurate and consistent annotation of ultrasound and other medical images is critical. Correlation of ultrasound images with images of the same body region obtained with other modalities (MRI, CT, mammograms, PET, etc.) becomes increasingly important for medical diagnostic and therapeutic purposes. As a result, precise positional registration of the targets is important.

This importance is illustrated by noting that finding a small tumor can save a patient's life. The smaller the tumor is before treatment, the higher the probability of long term patient survival or cure; however, a small rumor is difficult to find in a patient's body and differentiate from other structures or artifacts in the same region. Many times a suspicious small finding can coexist is the same region with multiple benign findings (cysts, solid benign nodules, etc.) with similar appearance, which may create confusion during a follow up exam and may lead to missing the suspicious lesion. As imaging diagnostic devices provide ever greater detail and sub-millimeter resolution, accurate position registration and mapping of lesions is becoming increasingly important in order to take advantage of the increased capabilities.

Ultrasound procedures are highly dependent on the device users experience and training. Position recording of certain findings is important, especially for the small targets and/or multiple targets. Most frequently, an ultrasound user will hold the ultrasound transducer in one hand and use the other hand to operate the ultrasound machine controls. It is desirable to obtain the instant recording of target coordinates seen in the ultrasound image in relation to the anatomical reference (for example, a nipple) and the simultaneous recording of the transducer position. Currently, the automated recording of the transducer position in real time scanning is limited due to the motion of the pre-selected anatomical reference secondary to body and transducer induced motion. Therefore, it is desirable to continuously update the position of the anatomical references, or landmarks, and apply the correction to the obtained measurements.

The American College of Radiology (ACR) recommends that all ultrasound images be properly labeled. For example, for breast ultrasound images, the findings position, in clock face position, distance from Nipple C and ultrasound probe position and orientation should be displayed with the ultrasound images. Currently, ultrasound findings are manually labeled by an operator, which is time consuming and prone to errors. Manual labeling involves the typing of an approximate position in the organ or part of the body, since an accurate position registration is time consuming and, importantly, difficult for the user.

A significant shortcoming in ultrasound mapping is the reproduce-ability of target location from exam to exam. A patient's body position, including soft tissue which is subject to movement, with respect to the examination table and position guides, and the ability to track transducer location in a reproducible format are limiting factors in the accurate examination of a patient. This inaccuracy can lead to inaccurate diagnosis and, importantly, inaccurate lesion description is a comparative examination. This, in turn, leads to ambiguities in the ability to definitively gauge the growth of a lesion or, critically, the success of treatment.

There is need, therefore, for a sensor attachment for three dimensional ultrasound mapping that enables increased accuracy in positioning during ultrasound examination. The present invention provides such a device.

III. OBJECTS AND ADVANTAGES OF THE PRESENT INVENTION

It is an object of the present invention to significantly reduce the time of ultrasound examination. It is a further object of the present invention to obtain the accurate position of selected targets in ultrasound images in relation to set reproducible body reference(s) with the corresponding ultrasound probe and patient's body position and orientation when selecting the target in the ultrasound image at the time of examination or at a later date in the stored images with attached positional information in both 2D or 3D imaging techniques.

It is yet a further object of the present invention to eliminate or minimize errors due to inaccurate positioning and position labeling, therefore reducing the risk of costly lawsuits due to missed diagnosis and decrease the number of callbacks for the patients for repeat examination.

It is yet a further object of the present invention to provide a sensor attaching device to enable accurate sensor placement and adherence and to, further, reduce the chance of operator error.

Among the many advantages that will be appreciated by those skilled in the arts is that the present invention provides an easy, uniform, method of positioning a patient for accurate examination of a target, especially with respect to follow-up or comparative examination, and communicating the target position among healthcare providers by guiding the ultrasound to a previously recorded target through following the real time display of the ultrasound transducer position in relation to the target coordinates from a previous examination.

IV. SUMMARY OF THE INVENTION

The present invention provides an apparatus and method of use for a sensor attachment for use in automated ultrasound probe position registration. The present invention comprises an apparatus for placement over a nipple and, optionally, a second or more sensor(s) for placement elsewhere, such as the sternum.

After initial, calibration and selection of one or more body references (nipple, umbilicus, skull, etc.), positional information associated with each individually recorded image frame or each image in a cine loop is stored with the corresponding image. Using a pointing device with the system display, spatial numerical coordinates of the selected pixel or region, including the distance from the anatomical reference, depth, angle to the body axis and a graphical representation, are displayed next to the ultrasound image. Also displayed are the real time position of the ultrasound probe and ultrasound image and target position over a body diagram or mark shown next to the real time ultrasound image, providing orientation help for the ultrasound operator. The corresponding body position relative to the exam table can be calculated, displayed in real time and stored with each ultrasound image.

Each saved ultrasound image or set of images in a cine loop can have attached the positional information needed to calculate each pixel's position to selected body references, the body diagram or mark, with the ultrasound probe position and orientation to selected body reference(s), the patient's body planes orientation on the exam table. All of the above information or any combination of data can be calculated, displayed and stored. In one embodiment, the anatomical reference sensor (48) can be applied at the nipple of the breast (C) when the corresponding breast is examined with the ultrasound machine. Other body parts or regions can be recorded with corresponding body reference points, for example: liver with umbilicus, neck with thyroid cartilage etc. Target pixel selection can be made during scanning at the time of the image capture, before saving the image, or at a later time at the review station.

During future examinations, the user can be guided to the target by entering the target coordinates obtained at the previous examination, display the target in the body diagram and adjust the probe position in the real time body diagram to overlap the target.

For the accurate automated recording of body targets and probe position related to certain body references, a user continuously obtains positional information from the selected anatomical references and the probe positional coordinates are instantly updated.

This is achieved by continuously monitoring the selected body reference(s) position, which in the preferred embodiment can be achieved with a position sensor like a magnetic type sensor, placed next to the body reference on the skin. In an alternate embodiment the body reference tracking can be obtained with an overhead tracking system using digital infrared or optical cameras with or without skin markers. In this embodiment, one camera can be used, or two or more cameras can be also used to achieve a three dimensional stereoscopic effect.

The TDMD can also be used to record multiple ultrasound, free hand 2D frames in a video sequence (clip) or cine loop, with each frame saved with the positional coordinates as described above. When using the positional information in the multiple 2D frames of one or more video sequences corresponding to a scanned volume, the 2D images can be reconstructed in 3D volume images corresponding to the scanned region, using known 3D reconstruction algorithms. The 3D volume reconstruction can be obtained from the original captured 2D ultrasound images or the segmented or otherwise processed 2D images in a video sequence.

This embodiment is well suited for ultrasound breast cancer screening or diagnostic breast ultrasound exams and can also be applied to other regions in the body like, but not restricted, to the eye, liver, abdomen, neck, kidneys, etc. The positional tracking of the body references, including the body planes position can be combined with the positional tracking of any type of ultrasound probes, including but not limited to 2D and 3D hand held probes, automated 2D and 3D ultrasound probes.

The main role for generating and recording the positional annotations associated with targets in the ultrasound images is to help the target relocation at subsequent exams. One condition to assure accurate and reproducible positional mapping of lesions is to have reproducible positional mapping of the selected body references.

A sensor attaching device or part may be employed to assist in the reproducible positioning and adherence to skin of the magnetic sensors, or other type of positional sensors at body references, to reduce the mapping errors due to differences at the repositioning of sensors and also prevent the interference with the scanning procedure from the sensors' connecting wire. The sensors can be of a variety of shapes, including but not limited to, a generally cup or cone shape for fitting over a nipple and a disc shape for placement at marker points such as the sternum.

There has been outlined, rather broadly, the more important features of the invention in order that the detailed description thereof that follows may be better understood, and in order that the present contribution to the art may be better appreciated. There are, of course, additional features of the invention that will be described hereinafter and that will form the subject matter of the invention.

V. BRIEF DESCRIPTION OF THE DRAWINGS

FIG. 8A illustrate a representation of patient's planes in the reference frame of FIG. 8.

Figure 24:
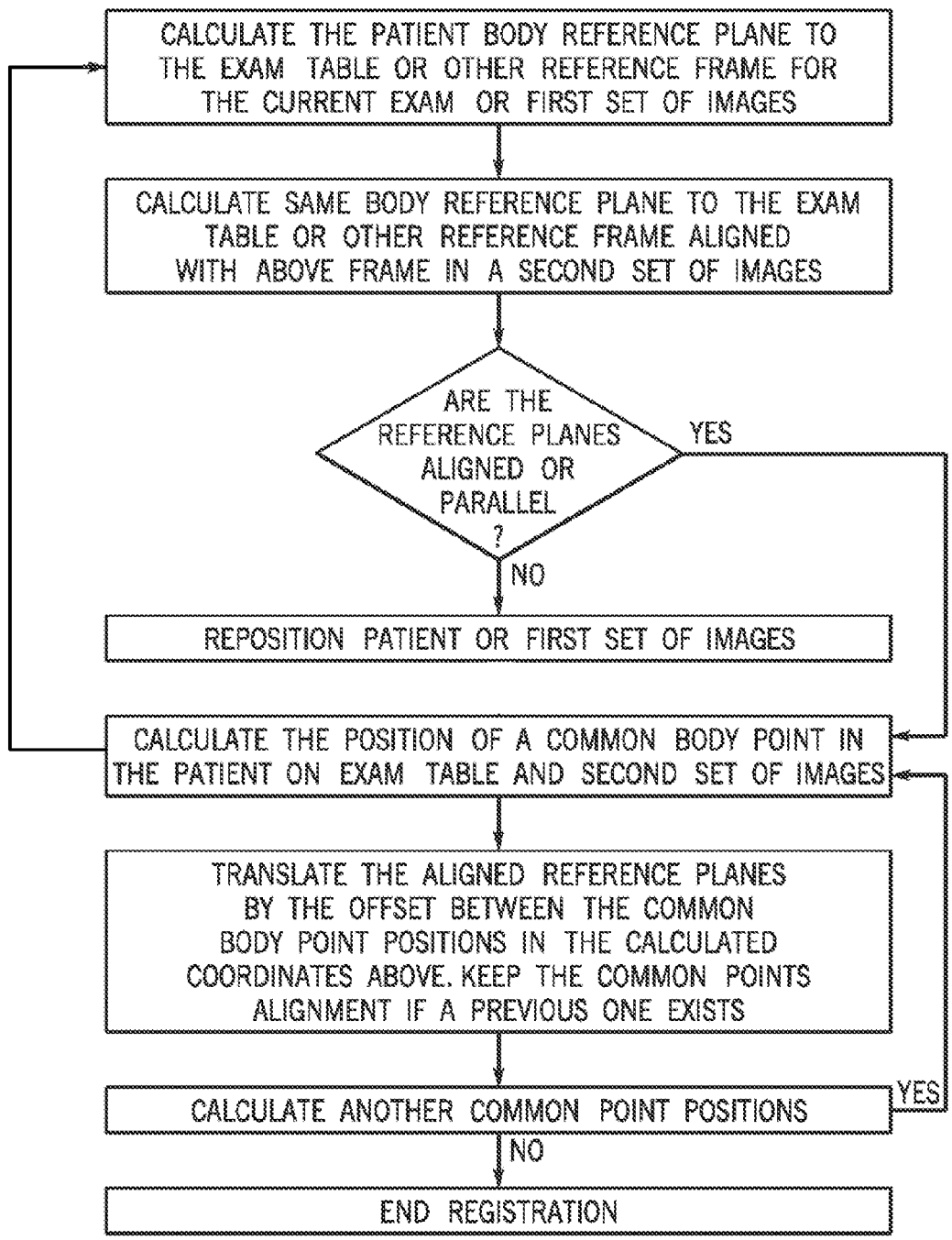

FIG. 24 describes the steps needed for the positional registration of the patient's body on the exam table or first set of images and a prior second set of images with the body planes calculated with the skin sensors and images position data.

VI. DETAILED DESCRIPTION OF THE PREFERRED EMBODIMENT

Before explaining the preferred embodiment of the present invention in detail, it is to be understood that the present invention is not limited in its application to the details of arrangements of the components set forth in the following description. As will be appreciated by those skilled in the arts, the present invention is capable of other embodiments and of being practiced and carried out in various ways. Also, it is to be understood that the phraseology and terminology employed herein are for the purpose of description and should not be regarded as limiting. It is also to be understood that where ranges are provided for various aspects of the invention and tor examples, they are approximate ranges and are not to be limiting except where noted otherwise.

Figure 1:
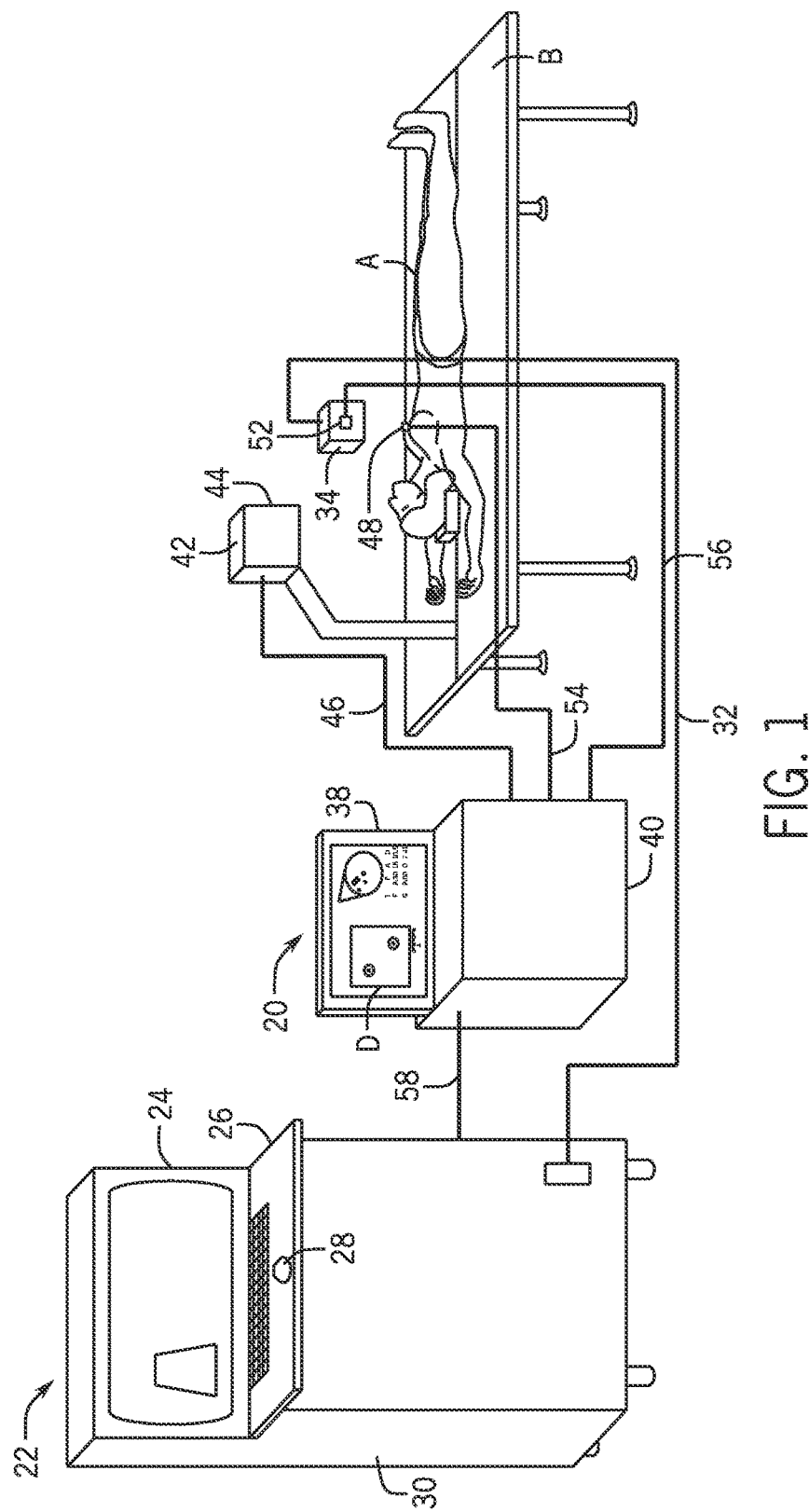
FIG. 1 depicts an overview illustration of the inventive apparatus placed in an ultrasound system.

Turning to FIG. 1, an over view of the physical aspects of an ultrasound device employing the inventive apparatus 20 is seen. Ultrasound machine 22 is a standard device including display 24, interface with keyboard 26 and pointer 28, chassis containing operating hardware (not seen) 30, probe connecting cord 32, and probe 34.

Figure 7:
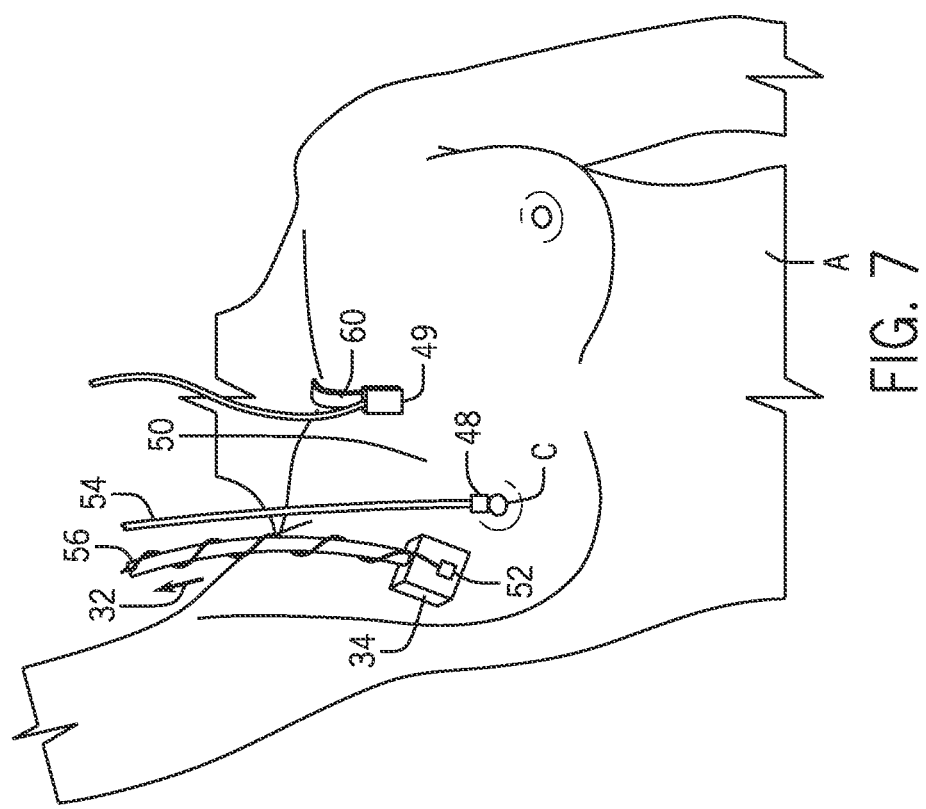
FIG. 7 depicts the inventive apparatus in a breast ultrasound examination with one sensor attached at the nipple and one sensor attached at the sternum.
Figure 8:
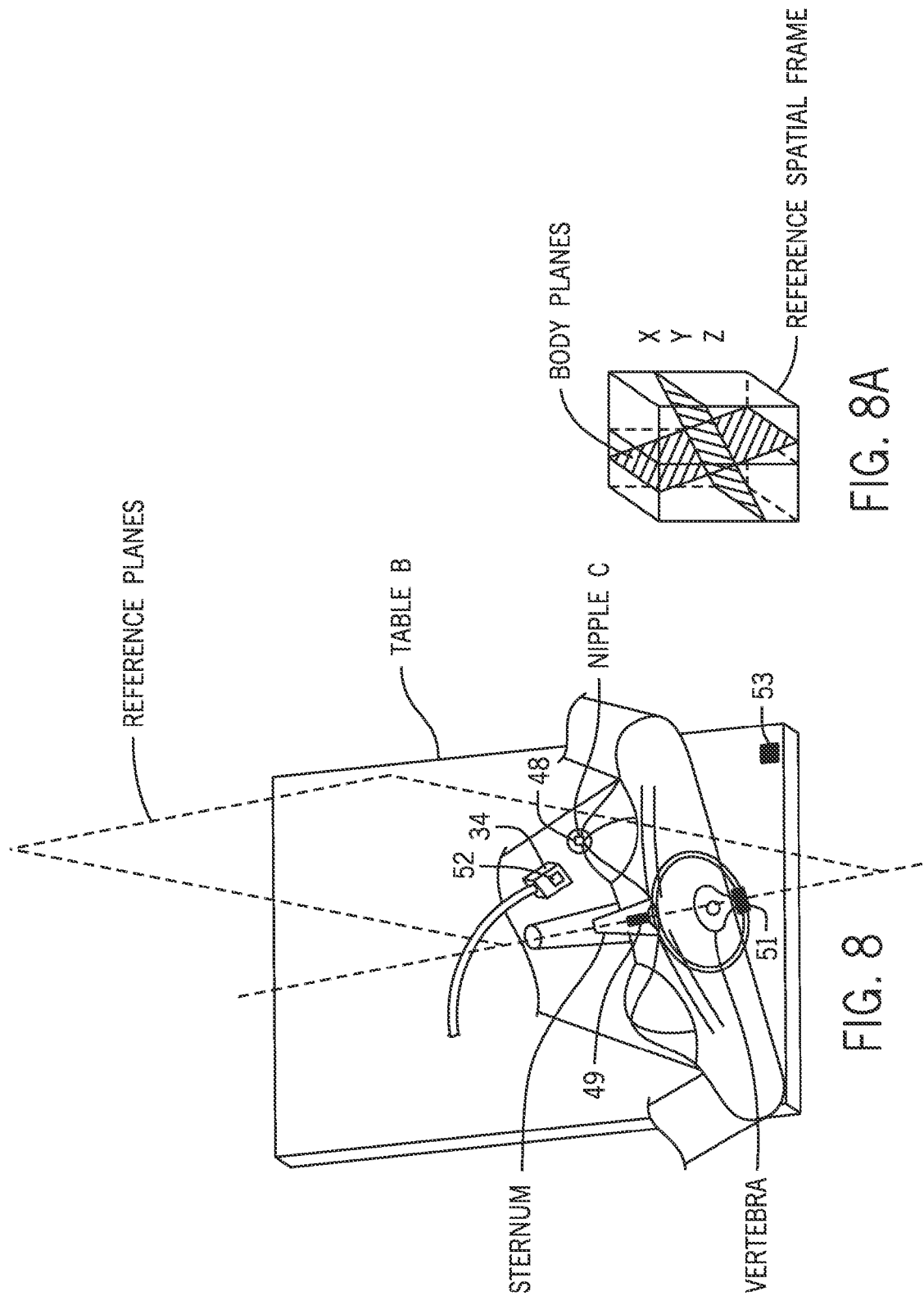
FIG. 8 shows the patient's body representation on the exam table with the position sensors attached to the sternum, back and a breast nipple.

Inventive apparatus (also referred to as three dimensional mapping display, or TDMD) 20 is depicted and comprises TDMD display 38, TDMD Chassis 40 containing hardware (also referred to as a "processor") and software (not seen; described in detail below), 3D magnetic tracking member 42 with the transmitter 44 connected to TDMD 20 by 3D magnetic tracking member cord 46, first magnetic sensor 48 connected to TDMD 20 by first magnetic sensor cord 54 and second magnetic sensor 52 connected to TDMD 20 by second magnetic sensor cord 56. A $3^{rd}$ and 4th position sensors, 49, 51 can be attached to track the patient's body position in reference to the exam table (FIGS. 7, 8). The position sensors may also be of a wireless variety, thus sensor cords 56, 58 would not be required. Also a combination of wired and wireless position sensors can be used to provide the position tracking module with positional information from the tracked anatomical references and the ultrasound probe or probes. (For completeness in explaining FIG. 1, Patient A is situated on examining table B.)

Figure 2:
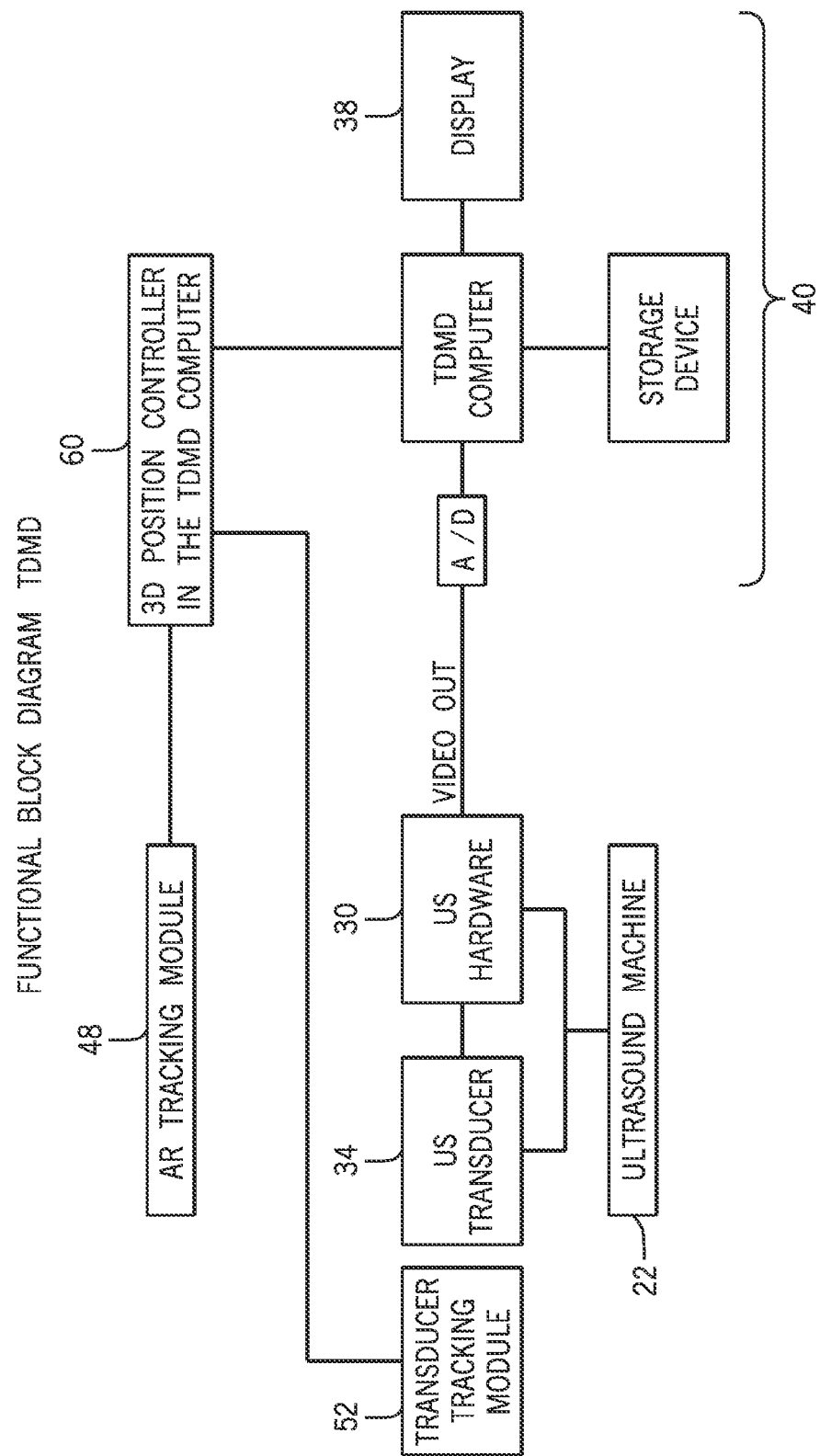
FIG. 2 illustrates the functional block diagram for the inventive device preferred embodiment with magnetic sensor used for body references and ultrasound probe tracking.

Turning to FIG. 2, a block diagram illustrating the various general working aspects of inventive device 20 are shown. All or any of the body reference magnetic sensors 48,49, 51 and the ultrasound probe magnetic sensor 52 provide the positional information to the TDMD 20 3D position board/module 60 (not seen). Video output 24 from ultrasound device 22 is digitized by the dedicated TDMD module/board 40. It should be noted that the analog to digital image conversion may not be needed if the ultrasound machine can be interfaced and it can directly provide the digital images to the TDMD 22.

TDMD can continuously track one or several body reference markers, which can increase the overall accuracy of the system. If multiple attached positional body markers or sensors are used, all of them or only some of them can be continuously or intermittently tracked.

To ensure reproducible and accurate mapping of the ultrasound images, magnetic sensors 48, 49 and 51 should be attached at well-defined and reproducible sites, outside or inside the body, during repeated ultrasound exams. Magnetic sensors 48, 49, 51 and 52 may be used simultaneously or angularly. It should also be noted that the TDMD could accommodate additional positional sensors as well.

Figure 10:
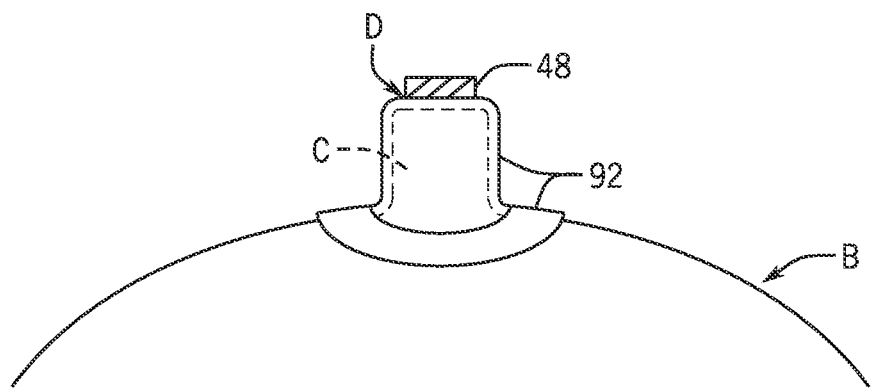
FIG. 10 illustrates a representative sensor nipple attachment system with a wireless sensor or marker and the attachment part to the skin.

As a non-limiting example, in the case of a breast ultrasound exam, to obtain reproducible mapping results, the magnetic or other position sensors should be attached to the Nipple C and monitor the position of the same point at the nipple, for example, the nipple center at the skin level, during repeated ultrasound exams. For instance, the center of the Nipple C top surface D can be the point of attachment for the anatomical reference position sensor (FIG. 10). It is desirable to have the magnetic sensor wire 54 outside the region of interest to be scanned. Continuing with the breast ultrasound exam example and with a magnetic sensor at the Nipple C, if magnetic sensor wire 54 is aligned in a direction perpendicular to the breast's coronal plane or a transverse plane through the nipple, the entire breast surface may be available for scanning, without the magnetic sensor wire in the path of the ultrasound probe 34.

To address the above, a sensor attachment device 92 may be employed to aid the attachment of a wired or wireless position sensor to the Nipple C. Sensor attaching device 92 can be built as a disposable part or as a reusable part after sterilization.

Figure 11:
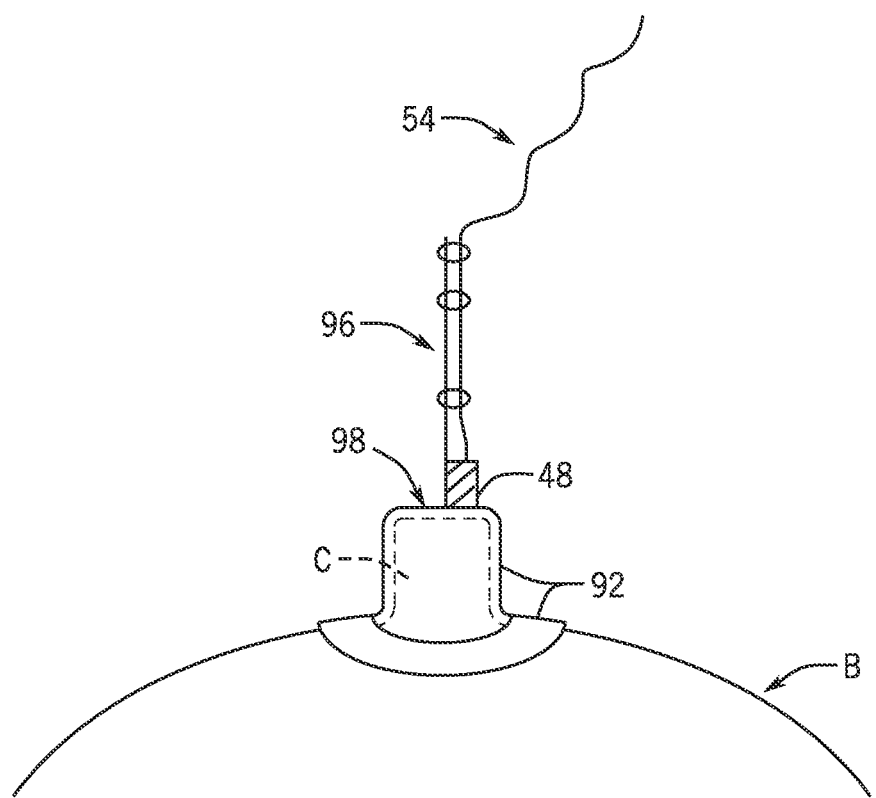
FIG. 11 illustrates a representative sensor nipple attachment system with a wired sensor or marker and the attachment part to the skin.

In one preferred embodiment sensor attaching device 92 may be shaped like a cup covering the Nipple C or any other similar shape covering the Nipple C. The sensor attaching device can be applied over the Nipple C and firmly attached to the Nipple C or areola skin with a skin compatible adhesive or tape. Turning to FIG. 10, magnetic sensor 48 is firmly attached at the top of nipple cover 92 For the wired sensors, in FIG. 11, a thin firm or flexible stick or tube 96 can be attached to the top 98 of the cover 92 and the wire 54 is attached to or included in the thin stick or tube 96, to hold the wire relatively perpendicular to the breast coronal plane and prevent obstruction of the ultrasound probe 34 path over the breast skin.

Figure 12:
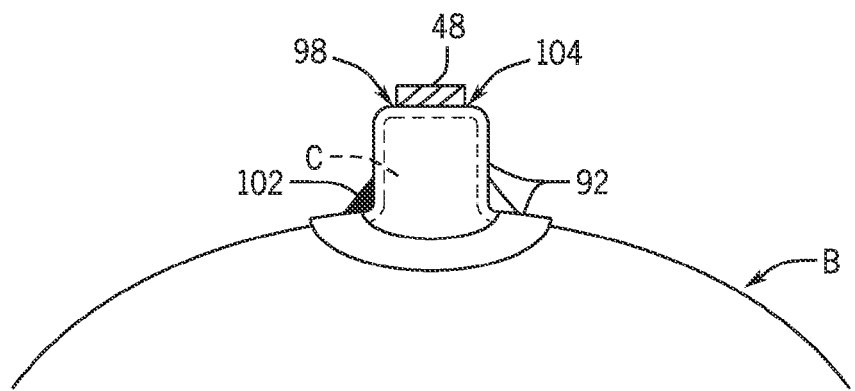
FIG. 12 illustrates a representative sensor nipple attachment system with a wireless sensor or marker and the attachment part to the skin with an orientation mark.

In an alternate embodiment, sensor attaching device 92 includes orientation markers 102 which enable positioning of the sensor attachment device with the markers having the same orientation during repeated exams, (FIG. 12). As depicted in FIG. 12, optical or infrared reflector(s) or emitter(s) are used to track the nipple C position instead of a magnetic sensor, 48, and is attached to the upper surface 104 of sensor attaching device 92 for the use with overhead optical or infrared cameras embodiments of the invention, FIG. 3. The protruding stick or film tube 96 can be attached to the top or on the side of the cover 98 for the wired magnetic sensor 48

Figure 13:
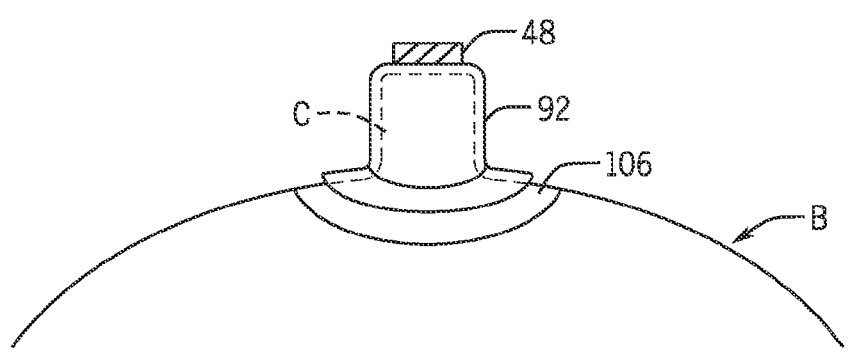
FIG. 13 illustrates another sensor nipple attachment system with a wireless sensor or marker and the attachment part to the skin.
Figure 14:
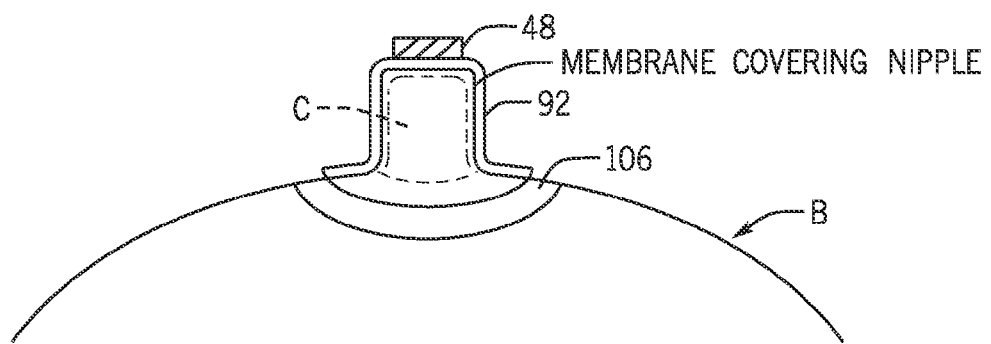
FIG. 14 illustrates another sensor nipple attachment system with a wireless sensor or marker and the attachment part to the skin.
Figure 15:
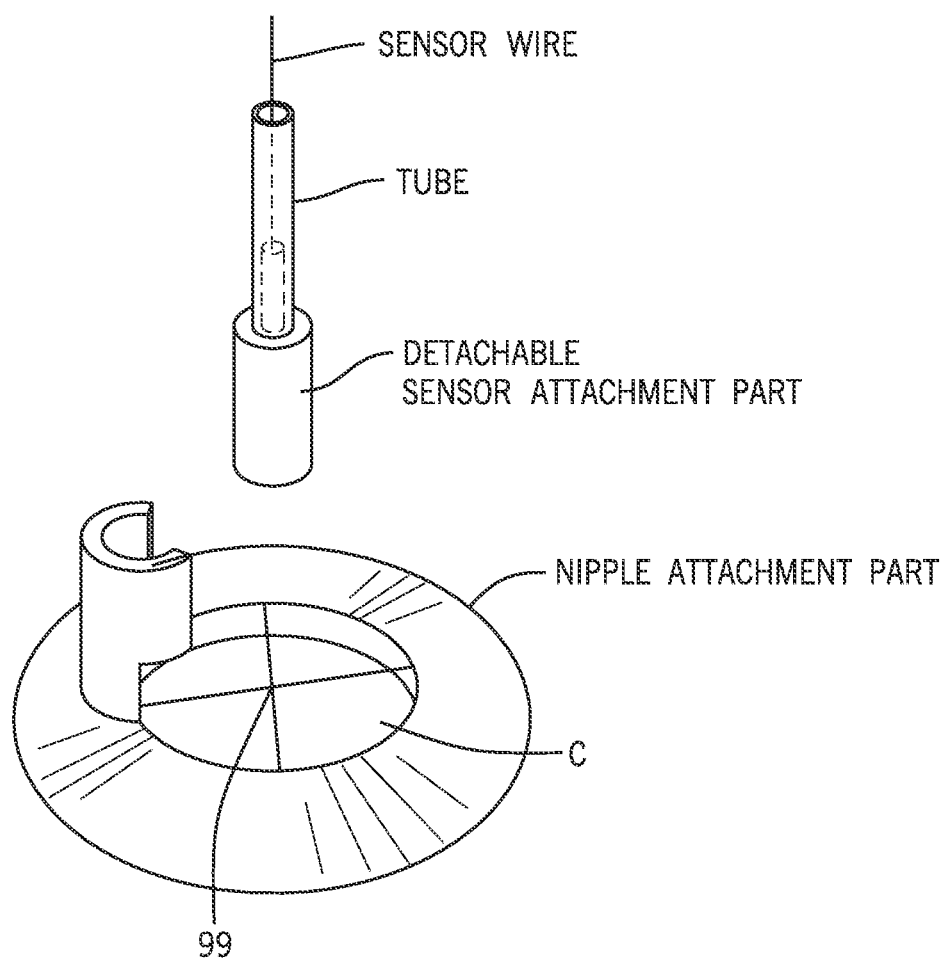
FIG. 15 illustrates a sensor nipple attachment system with a wired sensor or marker with a detachable sensor attachment component and the hollow disc shaped, attachment component to the skin, with cross hair marks for the attachment system calibration.
Figure 18:
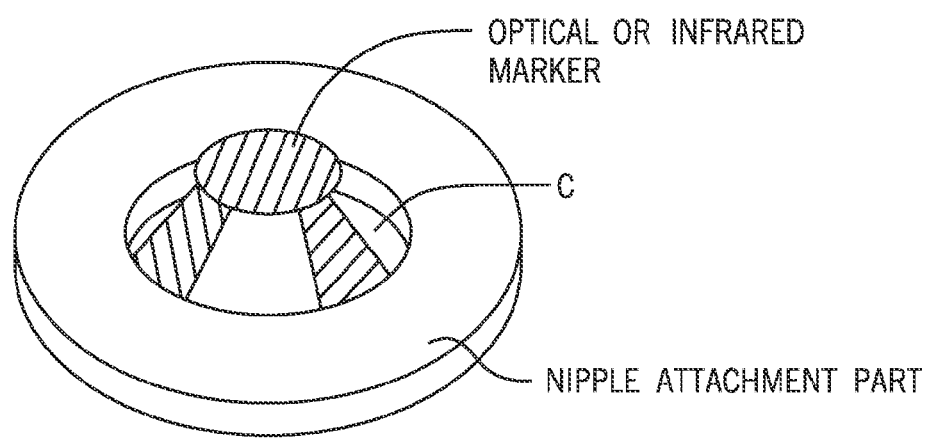
FIG. 18 depicts another hollow nipple attachment system for wireless sensors.

In yet another embodiment, and as depicted in FIG. 13, a hollow disc 106 is applied around the entire Nipple C or any part thereof and sensor attaching device 92 can then be applied to hollow adhesive disk 106 instead of directly to the skin. The sensor 48 with the nipple cover 92 can be attached to the adhesive disc directly, as depicted in FIG. 14. The hollow disc can be made from flexible tape when the nipple cover is attached to it (FIG. 14) or it can be made from a hard material when the sensor 48 is directly attached to it or to a protrusion above the disc (FIG. 15). For optical or infrared markers, the marker or markers can be applied above the nipple as shown in FIG. 18. All attachment device parts can be made from ultrasound transparent materials, to allow for a complete evaluation of the periareolar and retroareolar regions. The nipple attachment part can have a sensor attachment component and a nipple attachment component. The detachable component with the positional sensor can be made from a non-ultrasound transparent material (FIG. 15).

Figure 17:
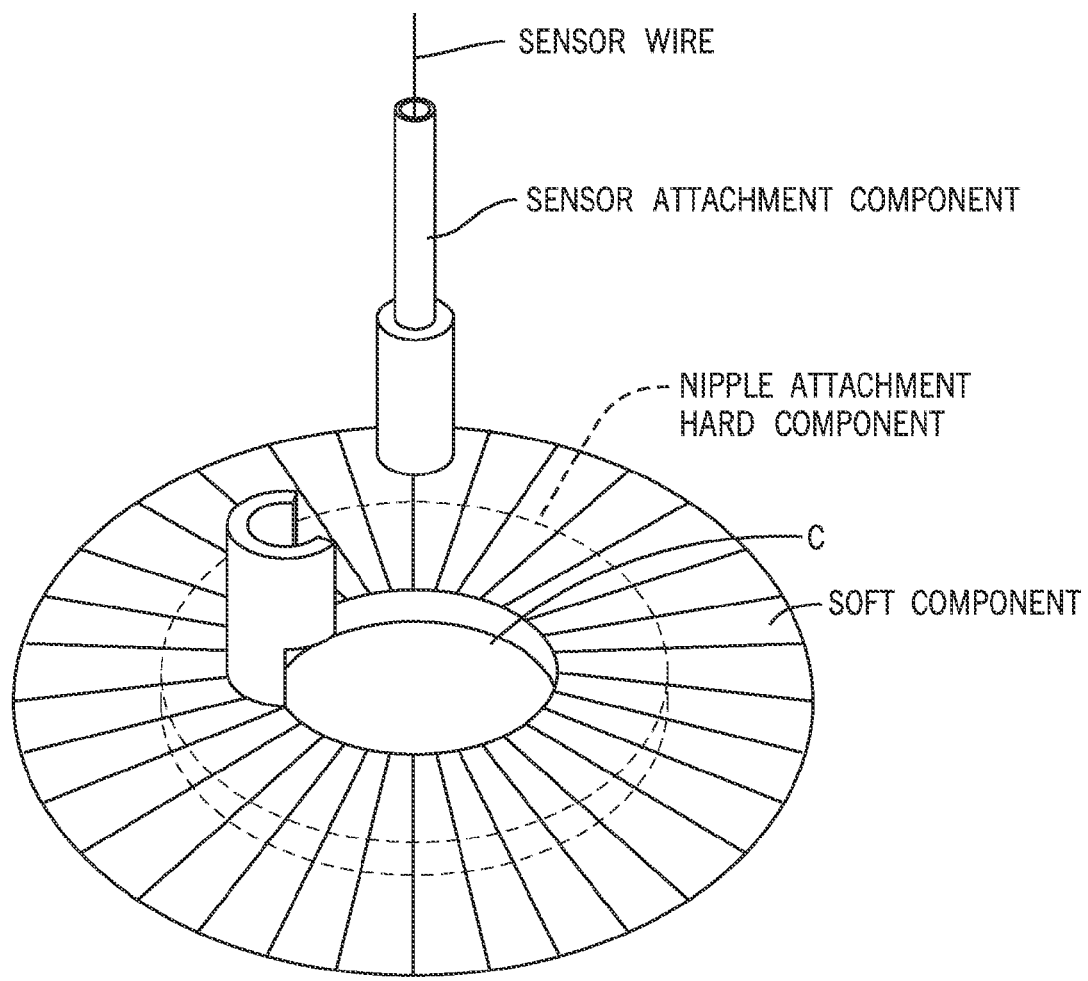
FIG. 17 illustrates a sensor nipple attachment system with a wired sensor or marker with a detachable sensor attachment component and the hollow disc shaped attachment component to the skin and a soft pad for enhanced acoustic coupling

For better acoustic coupling, to obtain good quality images of the retroareolar region, the part attached to the body skin can be covered or embedded in an ultrasound transmitting soft pad (FIG. 17). Any of the above described embodiments can have the soft pad attached to them.

All sensor or marker attachment embodiments can be attached to the skin with an adhesive material or using adhesive tape to cover the attachment part and adjacent skin. The adhesive material or tape can be ultrasound transparent, like Tegaderm™ (3M Corporation, St. Paul, Minn., USA) to prevent the interference with ultrasound images acquisition.

For practical use it would be difficult to have the AR tracking sensor in the nipple attachment piece positioned exactly at the center of the nipple, every time a patient is scanned. To address this limitation, the nipple attachment piece with the sensor (48) can be calibrated to track the nipple center point position in the 3D reference frame. In this configuration, the skin attachment part with the position sensor mounted on it and off the center of the nipple C, can be calibrated to monitor the Nipple C center position. For example, the center of the skin attachment part 15 hollow disc would match the nipple C center.

Figure 21:
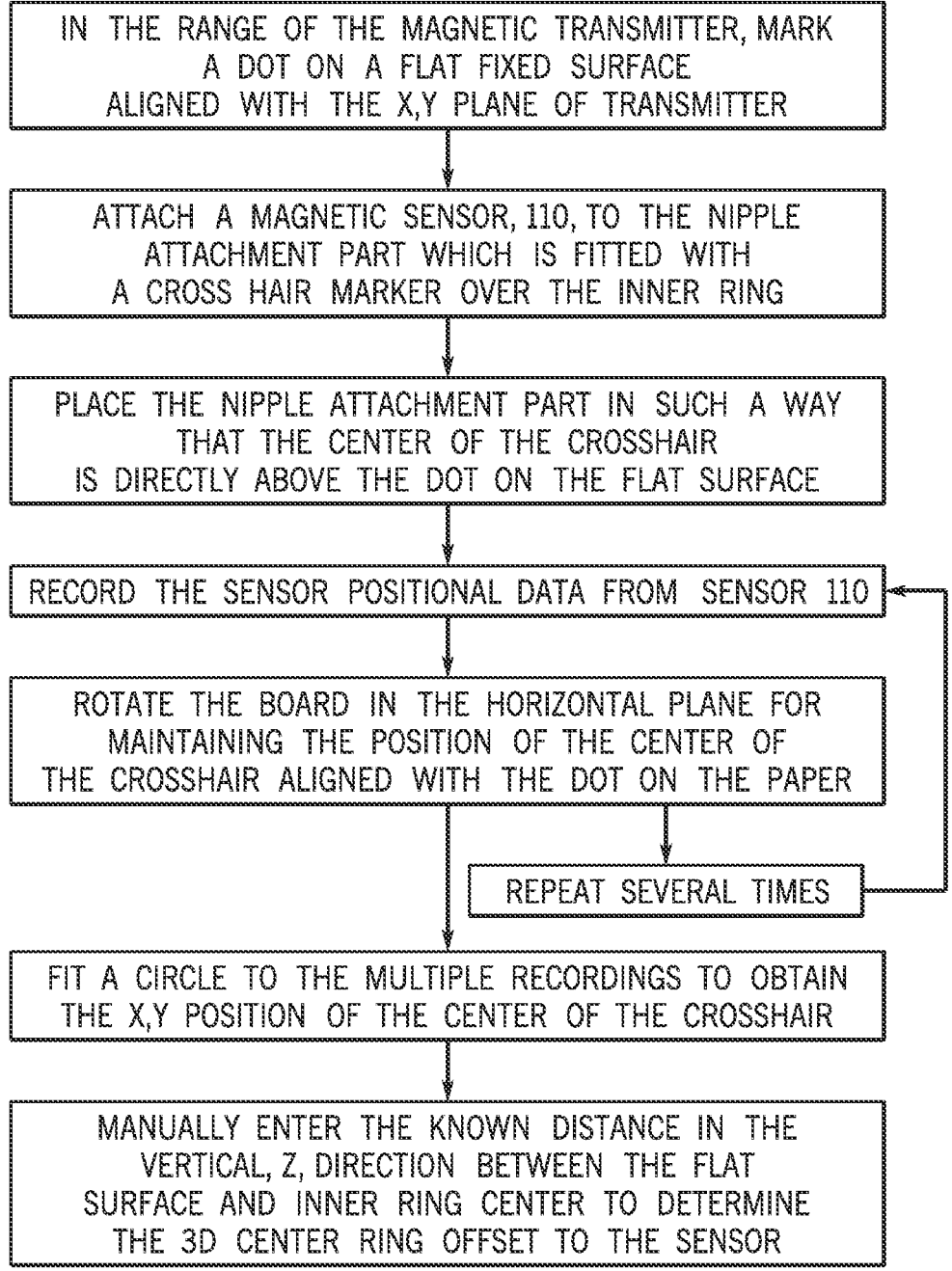
FIG. 21 shows the steps needed for the sensor attachment system calibration.
Figure 22:
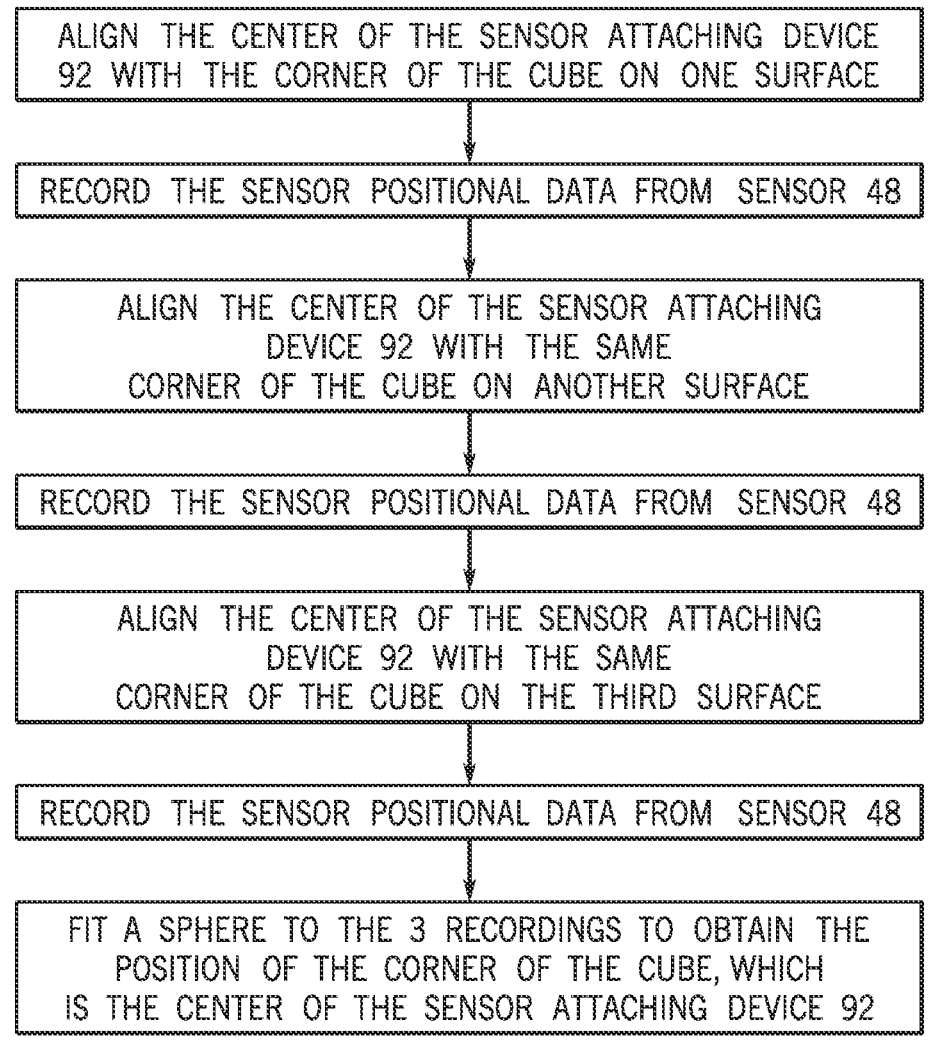
FIG. 22 shows the steps needed a different sensor attachment system calibration using a cube shape.
Figure 23:
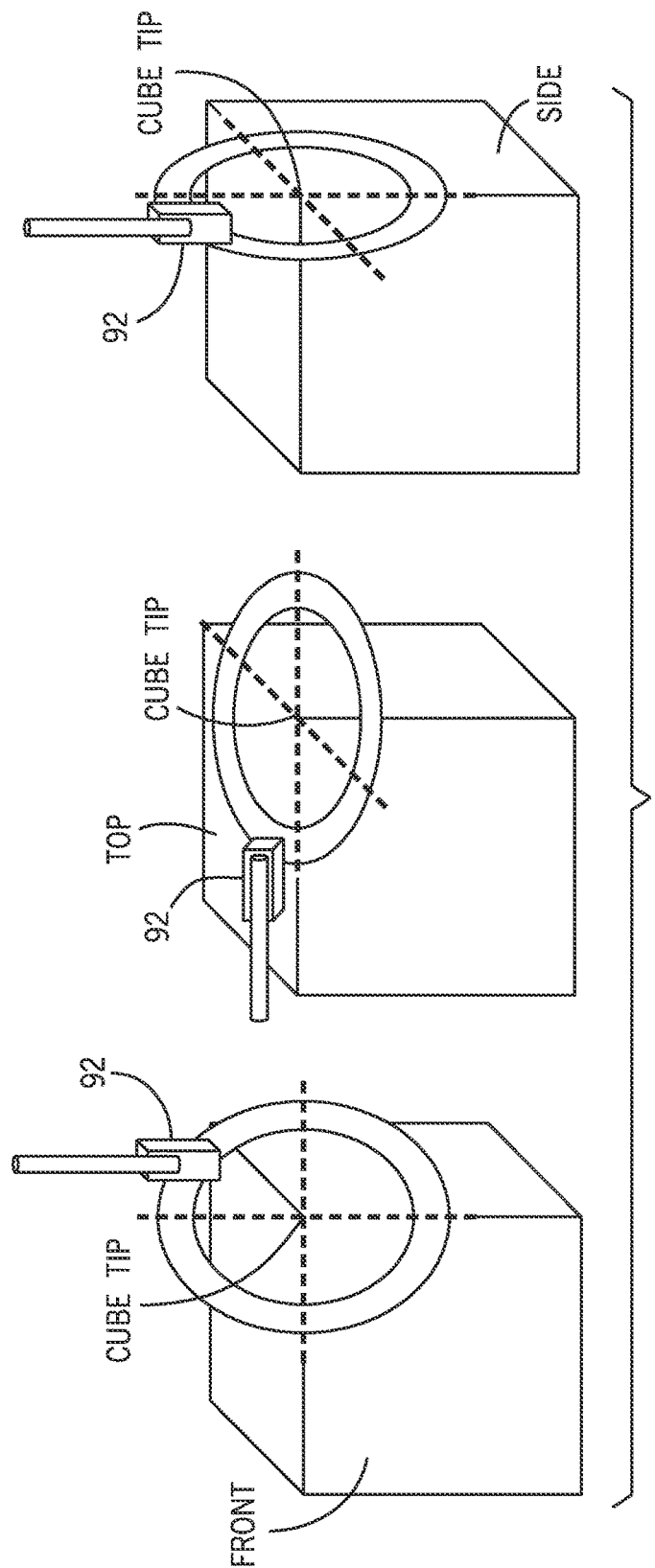
FIG. 23 shows the steps needed a different sensor attachment system calibration using a cube shape.

Such calibration of the skin attachment part can be performed using any method to perform a point or stylus 3D calibration in a reference system. For example, the nipple attachment component is fitted with a crosshair over the inner ring, with the cross point corresponding to the inner ring center which can be fitted over the nipple (99 in FIG. 15) and using the flowchart in FIG. 21. Such, a calibration can also be perforated using a solid cube as in FIG. 22 following the flowchart in FIG. 23. It is also understood that any combination of the above embodiments is possible and is part of the presented invention teachings.

During an ultrasound exam, the patients body position and orientation to the exam table or other fixed reference can change, which can have an effect on the position of the body internal structures when referenced to other body landmarks in a spatial frame and therefore have an effect on the measurement and description of a lesion's position. During the real time ultrasound exam image acquisition and capture, each internal ultrasound target position relative to the body references depends, among other factors, on the patient's position relative to the direction of the gravity force or the earth's magnetic field. Therefore the positional relation between the patient's body position and an examination table, B or other reproducible fixed reference used to position the patient, a chair or a wall for example, can be associated with the ultrasound images or other images of the body to aid repositioning the patient at subsequent imaging and match the gravity force effect between temporally distinct image sets. The gravity force effect is larger on deformable structures, like the breast. For example, during a breast ultrasound exam, the position of a small target in the breast relative to the nipple or other anatomical reference can change between the supine and half decubitus patient positions on the examination table. Unlike the approaches of the prior art, at the follow up exams or during the same patient exam, the patient whole body position can be adjusted to match the body position relative to the examination table or other known fixed reference object recorded with the previously obtained ultrasound images and match the position of internal targets referenced to body landmarks in previous images, therefore help finding a target with the previously recorded coordinates relative to selected body landmarks.

Figure 9:
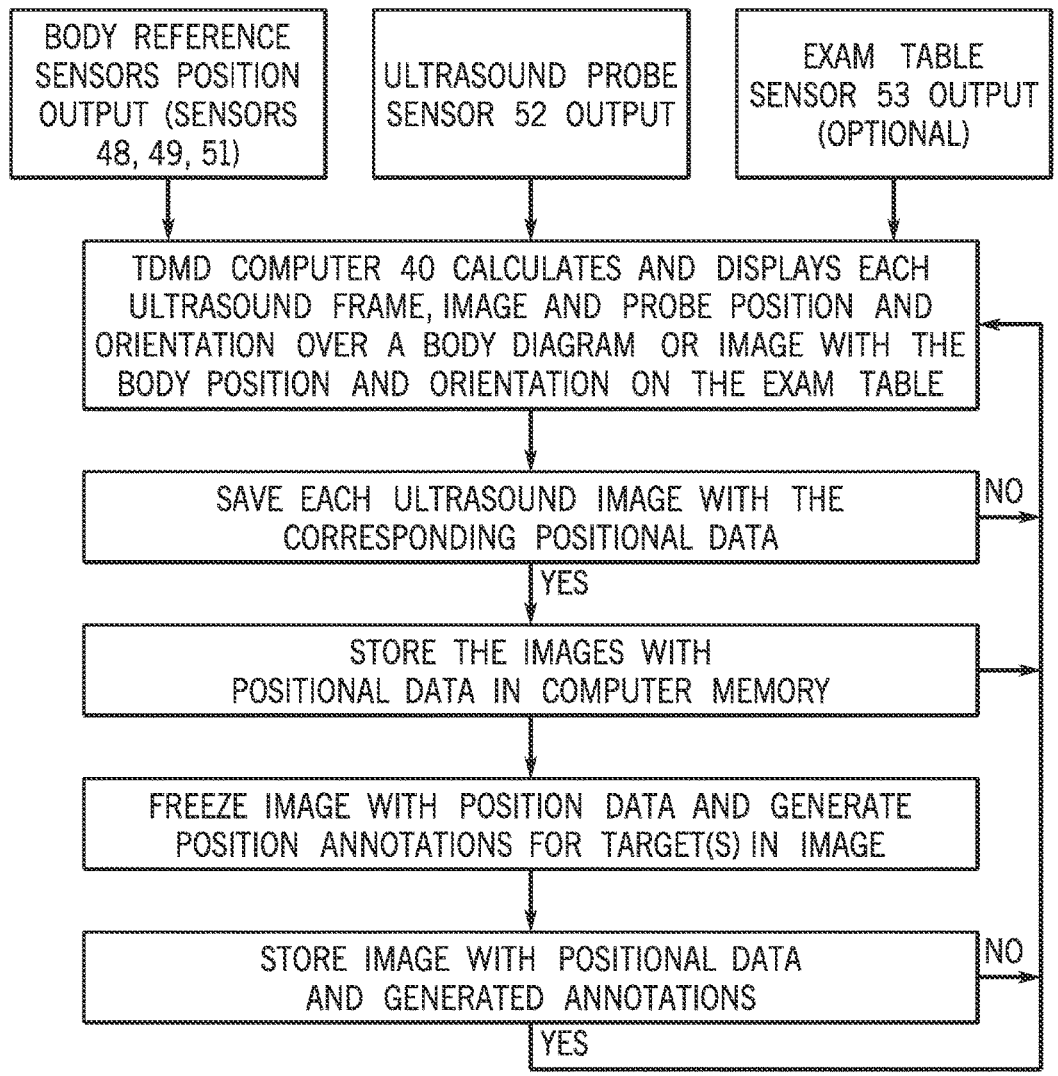
FIG. 9 illustrates the steps needed to select, measure, calculate coordinates, display and record the positional information of the ultrasound image and probe, patient's body position on the exam table associated with the corresponding diagnostic ultrasound images.
Figure 19:
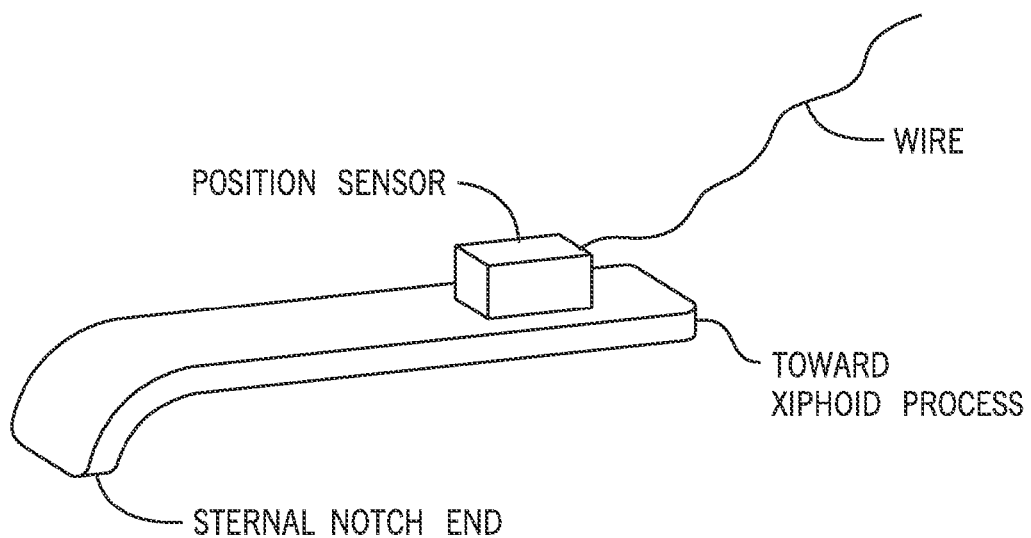
FIG. 19 illustrates a sensor body attachment system for the sternum with a wired sensor or marker and the attachment part to the skin.

To monitor the patient's body axes and planes in reference to an exam table, the body reference position sensor angles can be dynamically recorded and the values used to calculate the patient's body position related to the exam table (FIG. 9). However, to assure the body position to the exam table reproducibility at subsequent exams, the position sensor(s) tracking the body position would need to be reattached to the body in the same position referenced to the body, as they were at the first exam. This is a challenging task since small angular differences in the sensors position on the body can generate significant changes in patient's planes and axes orientation and generate registration errors. For example a position sensor attached to the nipple could not be used to monitor changes in the patient's body position due to the breast's deformable nature and sensor position changes due to the ultrasound probe induced deformation, unrelated to the body position. To address the above, a different sensor, 49 and sensor attachment part can be used. The position sensor(s) can be firmly attached to a sensor attachment part which is calibrated to the sensor and designed to be easily repositioned in same position and orientation at the patient's body. In one embodiment, the attachment part for the body position sensor(s) is designed as a long profile with a curved end which can be placed and aligned with the sternum long axis with the curved end at the sternal notch or the xiphoid process of sternum. For example a magnetic sensor 49 can be attached to the sternum attachment part (FIG. 19).

Figure 20:
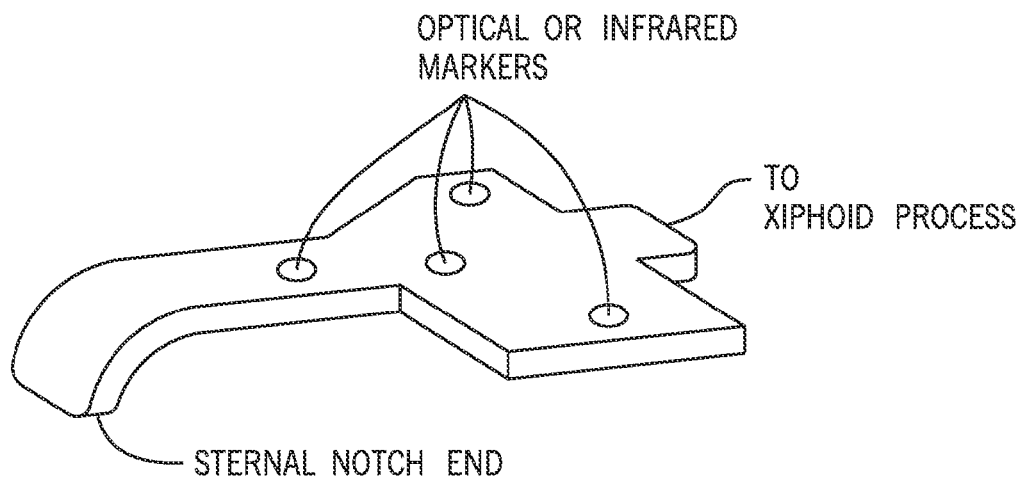
FIG. 20 depicts illustrates a sensor body attachment system for the sternum with a wireless sensor or marker and the attachment part to the skin.

In a different embodiment, dedicated markers can be used for optical or infrared position tracking (FIG. 20).

The sternum attachment can be calibrated to the attached position sensor(s), for example it can have the long axis or the attachment part's flat plane calibrated to the sensor. One or more points at the attachment part with the position sensor can be calibrated using the method explained in FIG. 21, 22, 23 or any other calibration method can be used. The calibrated body attachment part can be used to define lines or planes which can be aligned with the body planes and axes, to facilitate the attachment part reposition on the body. Once attached to the sternum skin, the calibrated attachment part and sensor can track the patient's body long axes and planes.

The sternum attachment part rotation around the long axis during patient's movement can induce errors in the body position tracking. To address this limitation, in a different embodiment, a different, fourth position sensor 51 (FIG. 8) can be attached at a reproducible position at the patient's body, for example the skin on the back, over a prominent spinous process of a cervical or thoracic vertebra. The exam table or other reference object can move during the examination, to compensate for the table motion during the patient's exam, a position sensor 53 (FIG. 8) can be attached to the table and any table position change in the position reference frame can be calculated from the sensor 53 output and applied to the other positional calculations for the body and ultrasound probe position and orientation. The table position monitoring is not needed when the spatial reference frame, the magnetic transmitter for example, is firmly attached to the exam table and would follow the table movement. The plane generated by the data processed from the calibrated sternal attachment part and sensor and the position sensor attached at a different body location, like at the back of the body over the spinous process of a vertebra will define a reference plane S, which is the sagittal plane in the used example. The reference plane S and sensors position can be tracked during the patient's exam and dynamically displayed with alpha numerical coordinates and graphical over the body diagram, mark or other body or body part representation as shown in FIG. 8. FIG. 8A illustrates a representation of the patient's planes in the reference frame of FIG. 8.

In yet another embodiment, the position of a second reference used in addition to the sternum sensor, like a vertebral spinous process, can be measured at one or several times during the exam with a position sensor attached to a calibrated object. An example is the calibrated ultrasound probe with a position sensor, by touching the shin over the selected landmark with a preset point of the calibrated object, like ultrasound probe scan surface center or margin. The reference plane of the body is recalculated at each measurement, in the example with the spinous process of a vertebra; the sagittal plane of the body position is recalculated at each repeat measurement.

In another embodiment, the position of a body reference, like the spinous process tip of a vertebra can be calculated from ultrasound images of the selected body reference. With the calibrated ultrasound probe, the selected body reference is scanned and single frames or sequential frames in a video clip can be obtained. The body reference pixels are selected in one or more images and the spatial coordinates of the selected pixels are calculated in the reference frame with the position data from the sensor attached to the ultrasound probe. The body reference pixel selection in the ultrasound images can be manual, by pointing to the pixels, semi-automatic or fully automatic with image processing algorithms dedicated for image analysis. To facilitate the imaging of superficial structures like the tips of a spinous process of a vertebra, tip of acromio-clavicular joint, xiphoid process of sternum or any other structure, a standoff pad with an ultrasound transmitting medium can be used.

Figure 16:
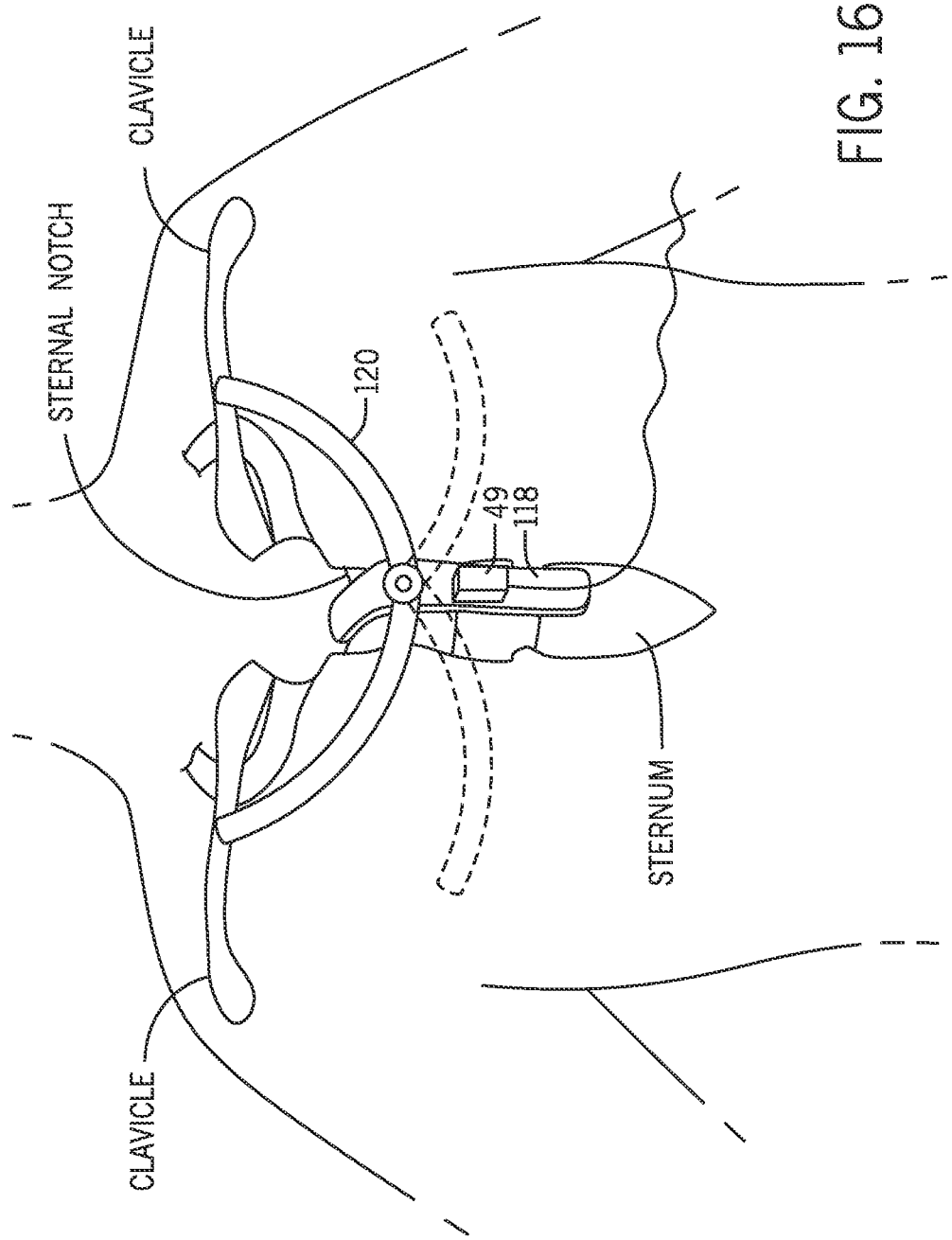
FIG. 16 illustrates a sensor body attachment system for the sternum with a wired sensor or marker and the attachment part to the skin.

In yet another embodiment, the sternum attachment part and sensor position relative to the body can be stabilized with two extensions 120, attached to the clavicles (FIG. 16). The extensions 120 ends can be taped at the clavicle and opposite ends firmly attached at the sternum attachment piece 118 or attached to a pin which allows the extensions to rotate to fit the overlaying with the clavicle bone in a range of anatomical variants (FIG. 16). The described methods to track a body position to a fixed reference can be performed alone or combined, also with one or more sensor (s) attached to any part of the body.

With the positional data from the sensors attached to the body, the patient's body axes and planes can be calculated dynamically in reference to the exam table or other 3D reference system. With one patient body plane defined in a positional reference system, other planes can be calculated and used to generate positional coordinates. For example, once the sagittal plane of a patient's body is determined and tracked, the coronal plane can be calculated and used for the clock face position coordinate calculation and display in a breast ultrasound exam. The position of a body diagram or other second set of previous images representing the body, with or without a first set of real time ultrasound images, referenced to the exam table, can be calculated using the body reference sensors output also displayed and stored on demand (FIG. 8).

The calculated patient's planes can be used to align the patient's body and ultrasound images during an ultrasound exam with one or more sets of previous images, for position registration purposes. The previous sets of images may be represented by 2D or 3D body marks or diagrams or medical images like MRI, CT etc. The body landmarks tracked with the sensors and the corresponding attachment parts can be identified in other sets of images and the position registration between the different sets of images can be performed. For example the sternal notch, clavicles and spinous processes of vertebrae can be easily identified in CT scan or MRI images, corresponding body planes can be calculated and aligned in the ultrasound set of images and the other sets of images, previously acquired.

Furthermore, when in a patient the same one or more body planes are defined in the first set of ultrasound images and in a different prior set(s) of images, by using same or different body landmarks as in the first set of images, the body position registration during the ultrasound exam can performed by aligning the known similar body plane(s) or axis(es) in the different sets of images, followed by the shift of the entire body volume of one image set to match one or more common body landmark points (FIG. 24).

Alternatively, any two different sets of images of the body with known similar orientation planes can be coregistered by aligning the planes and axes followed by shifting the entire aligned volume to one or more common body landmark points.

The advantage of this method of registration for different image sets is that it eliminates the need for multiple fiducial markers and allows the registration of body volumes when using different anatomical landmarks to define the body planes and axes position and orientation in space.

Figure 3:
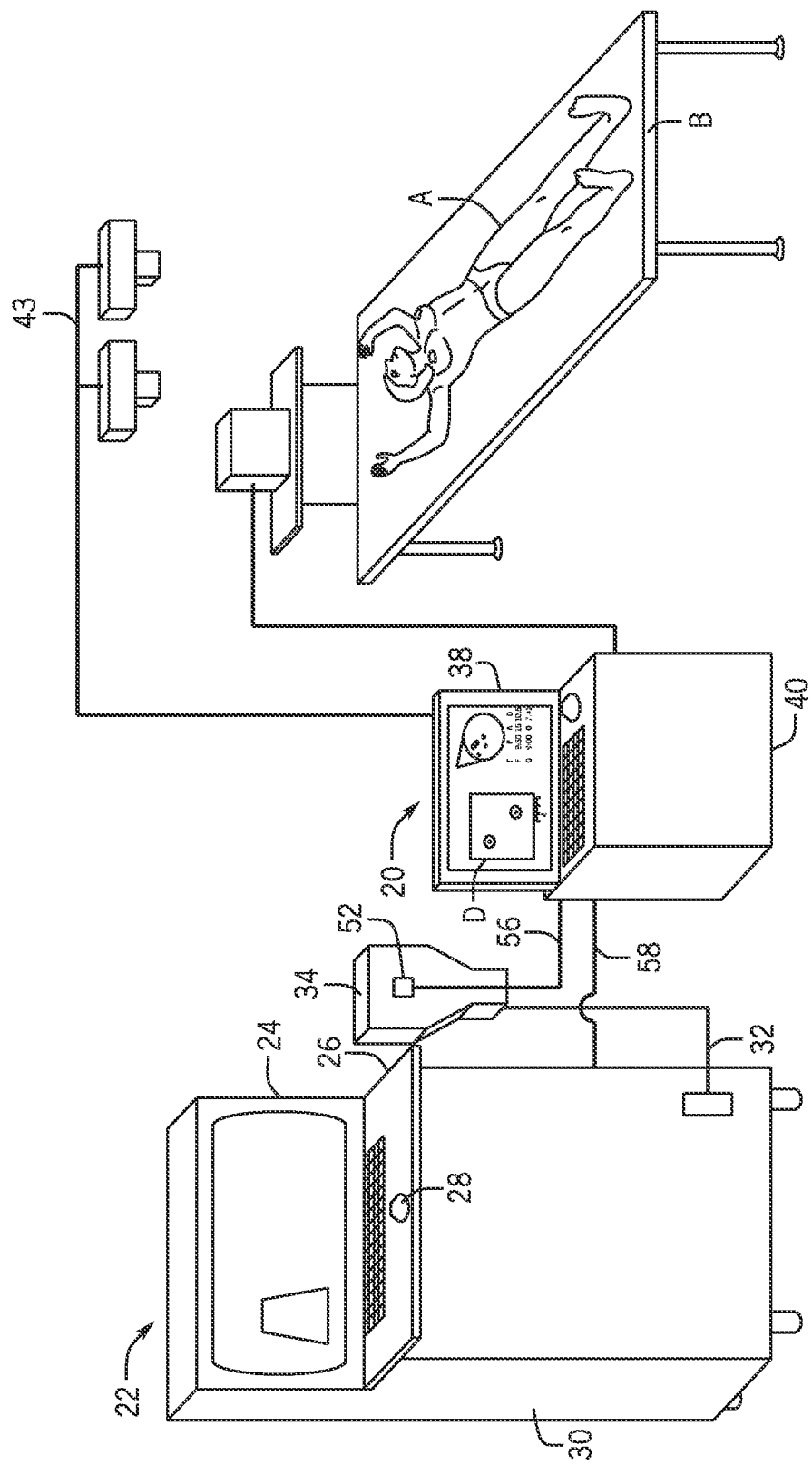
FIG. 3 depicts an alternate embodiment illustrating an overhead infrared or optical body reference tracking system.

Other configurations will work as well. For non-limiting example, FIG. 3 illustrates an alternate configuration in which second sensor 52, which can be optical, magnetic or any other type, provides the positional information associated with ultrasound probe 34 to the TDMD 3D position board/module 60. The overhead infrared or optical anatomical reference (AR) tracking system 43 provides the positional information to the TDMD computer 40. Video output 24 from the ultrasound device 22 is digitized by the dedicated TDMD module/board 40. Again, analog to digital image conversion is not required if the ultrasound device 22 can be interfaced and directly provide the digital images to TDMD computer 40. The digital ultrasound images with the associated positional information are displayed in the TDMD computer display 38 or stored for review and processing at a later time.

Figure 4:
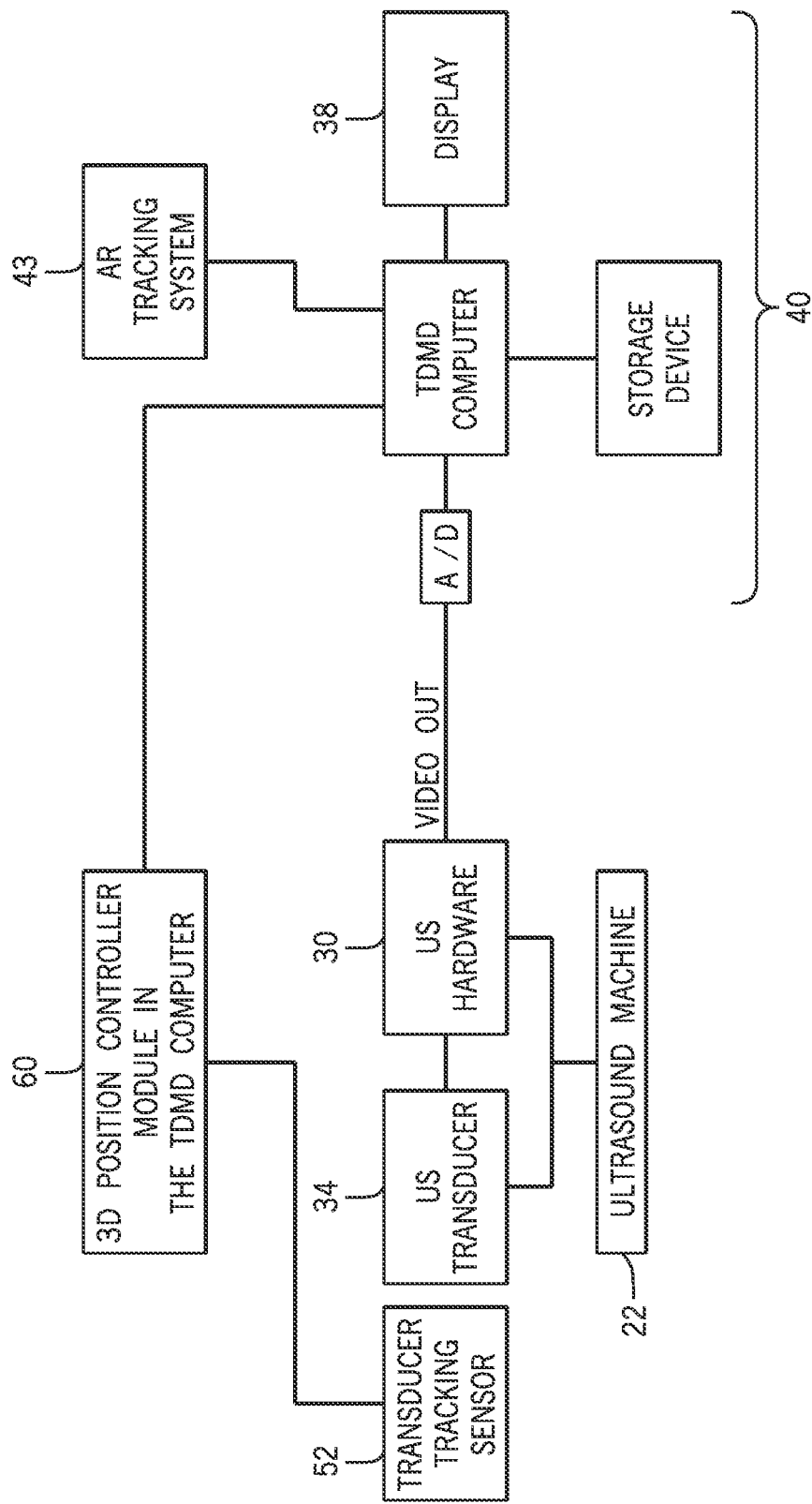
FIG. 4 illustrates the functional block diagram for the inventive device in the alternate embodiment with an overhead infrared or optical body reference tracking system.

Turning to FIG. 4, a block diagram illustrating the various general working aspects of inventive device 20 are shown. Second position sensor 52 attached to the ultrasound probe provides the positional information to the TDMD 20 3D position board/module 60 and overhead infrared position detector 43 transmits positional information to TDMD computer 40. Video output 24 from ultrasound device 22 is digitized by the dedicated TDMD module/board 40. It should be noted that the analog to digital image conversion is not needed if the ultrasound machine can be interfaced and it can directly provide the digital images to the TDMD 22. Also, and as will be appreciated by those skilled in the arts, sensor types can be mixed without interfering with the function of the invention and are meant to be included within the spirit and scope of the present invention.

Figure 5:
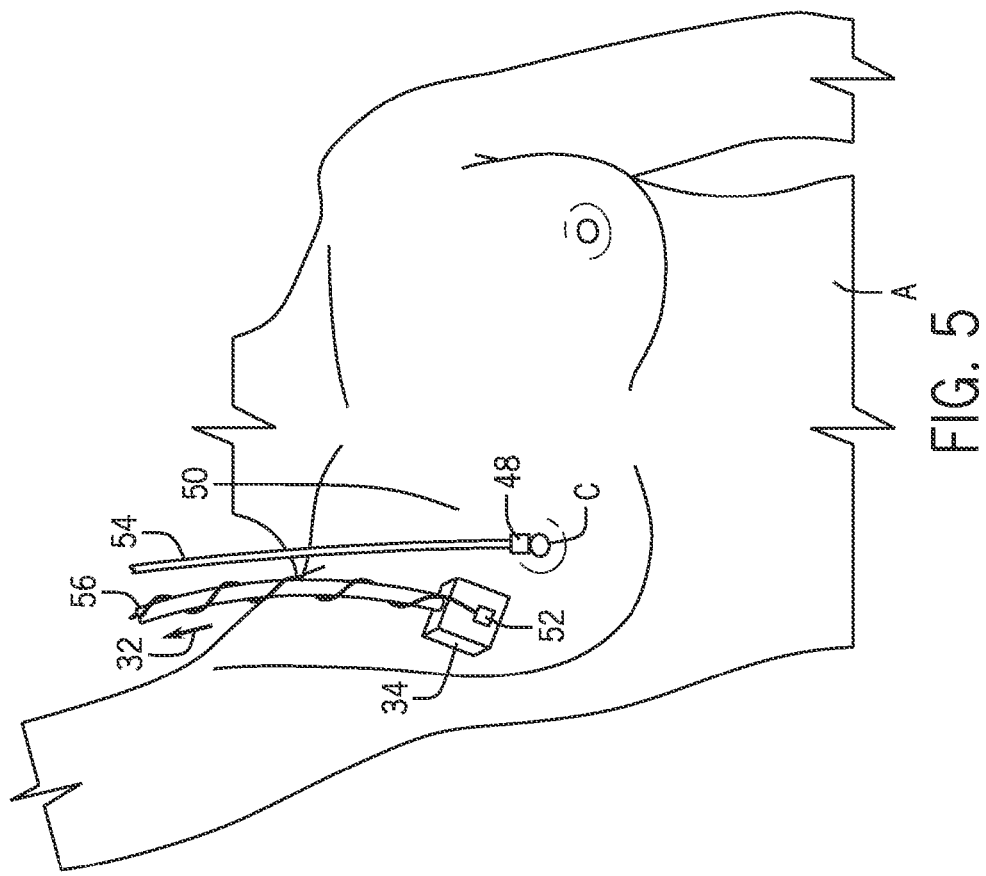
FIG. 5 depicts the inventive apparatus in a breast ultrasound examination with one sensor attached at the nipple.

Returning to FIG. 1, second position sensor 52 is attached to the exterior of probe 34 and, as seen in more detail in FIG. 5, first magnetic sensor 48 is positioned at the body reference, here, the breast nipple C of Patient A.

Ultrasound device 22 video output 24 is directed to TDMD video capture board at TMDS Chassis 40 through video output cord 58 as is 3D magnetic tracking member 42 through 3D magnetic tracking member cord 46. TDMS display 38 is then enabled to shows images D generated by ultrasound device 22 and associated positional data as collected from 3D tracking member 42, first sensor 48 and second position sensor 52.

Figure 6:
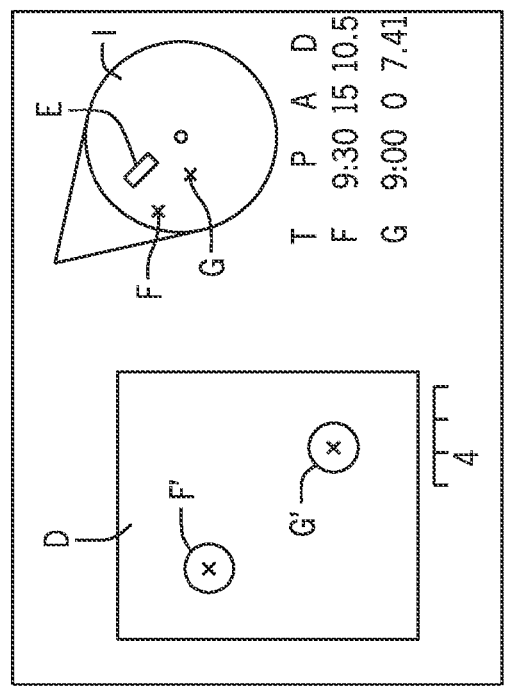
FIG. 6 depicts the image created during a breast examination as illustrated in FIG. 5.

Turning to FIG. 5, a detailed view of probe 34 with the second position sensor 52 and first position sensor 48 applied at the right Nipple C. First position sensor 48 continuously tracks the body reference position, the Nipple C in this case, to compensate for motion registration errors during the ultrasound exam. FIG. 6 illustrates TDMD display 38 with the captured video image D from the ultrasound machine and the body diagram of FIG. 5 with the probe 34 position and orientation at the time of image capture D and two different targets F and G in body part diagram I, and F' and G' as selected in image D image capture.

Additionally, each target is displayed with the associated position (clock face position or degrees to longitudinal axis and anatomical reference as center) and distance (cm) from the selected anatomical reference F and G. Positional coordinates are displayed under body part diagram 1 in FIG. 6. While the inventive device enable any number of coordinates to be displayed, here the example includes Target number (T), example F and G, Positional in reference to anatomical reference in hour format (here, 9:30 for F and 9:00 for G), position from anatomical reference point in degrees (here, 15° for F and 0° for G), and distance from anatomical reference point in centimeters (cm) (here, 10.5 cm for F and 7.41 cm for G). Also, probe 34 position location is identified at transducer position Icon E.

Additionally, an additional display function is to show a cumulative area of the transducer positions (via icon E) over the body diagram, where the ultrasound images were recorded during patient examination. This will allow for the quick evaluation of ultrasound examination completeness, at the time of the examination or at a later time.

In the preferred embodiment any off the shelf generic PC computer with Windows XP®, Windows 7 (by Microsoft Corporation, Redmond, Wash.) can be used to run instructions compiled in C++ and dotnet languages. While preferred, those skilled in the arts will understand that the invention can be implemented on any other computer platform and operating system.

The software to run the program is that incorporated by reference above. The software substantially used to process the data received by the processor form the at least one sensor and data from the ultrasound to manipulate the data for identifying, and storing in memory as selected by the user, target site location and size information in relation to selected anatomical reference points for simultaneous review and interpretation and later retrieval for comparative purposes with later examination, whether compared in real time or a later time based upon saved data. The inventive device enabling a user to accurately review, evaluate, and compare examination results by having anatomical reference point guides to isolate target sites.

The body diagram representation is not limited to the "bird's eye view" type like the "clock" representation for the breast, but more complex and realistic three dimensional representations of the body or body regions, including images obtained with other modalities like MRI, mammograms, gamma cameras or positron emission tomography and using contour rendering algorithms, can be used. The calculated and recorded positional data can be displayed in these representations. The ultrasound transducer position, orientation, can be depicted in a realistic appearance in space so it can be easily reproduced at subsequent examinations.

Additionally, the preferred 3D position registration system is based on magnetic tracking technology (for example, like that manufactured by Ascension Technology, Burlington, Vt.); however, any other suitable technology, such as optical or ultrasound, may be employed. Moreover, the inventive device can be deployed as an add-on to any existing ultrasound unit, and can outfit DICOM compatible and non-DICOM machines as well. The infrared sensors, also commercially available (Natural Point Inc., Corvallis, Oreg.), comprise at least one infrared cameras with the dedicated hardware and software receiving reflected infrared light from the reflectors or emitted infrared light from small infrared light sources applied over the anatomical references. The infrared cameras can be replaced with optical cameras and the infrared reflectors with optical markers. One or more infrared or optical cameras can also be used.

The ultrasound probe and anatomical reference point real time tracking is not limited to the above solution, but other tracking modalities like ultrasound, optical, inertial etc. can be used tor the ultrasound probe and optical/pattern recognition, magnetic, etc. for the anatomical reference point real time tracking. It should also be noted that tracking modalities can be used in combination with one another, for non-limiting example, ultrasound tracking with optical tracking. It is also notable that the described TDMD system and method can optionally be used with the anatomical reference tracking feature disabled.

In any of the above configurations, initial calibration is needed to register the ultrasound probe scanning plane orientation and position. Any 3D calibration method for 2D ultrasound probes, as available in the published literature can be used.

The preceding merely illustrates the principles of the invention. It will be appreciated that these skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

I claim:

1. An attachment system for one of a wired position sensor and a wireless position sensor comprising:
   an attachment member having an opening formed through a thickness thereof for placement around at least a portion of a breast nipple, the attachment member configured for attachment to the areola or nipple skin; and
   a position sensor comprising one of a position sensor wire and a wireless position sensor attached to one of the attachment member and a protruding member attached to the attachment member.

2. The system of claim 1 wherein the attachment member has a disc shape.

3. The system of claim 1 wherein the position sensor is coupled to a detachable component coupleable to the attachment member.

4. The system of claim 1 wherein the attachment member and protruding member are calibrated to the position sensor.

5. The system of claim 1 further comprising an adhesive configured to affix the attachment member to the areola or nipple skin.

6. The system of claim 1 further comprising an attachment system for a wired body position tracking sensor comprising an elongated component with a curved end configured to fit the sternal notch or xiphoid process.

7. The system of claim 6 further comprising a linear extension connected to the elongated component on each side at one end and configured to be attached to the clavicle on the same side at the other end, and a wired position sensor attached to the elongated component.

8. The system of claim 1 further comprising an attachment system for a wireless body position tracking sensor comprising an elongated component with a curved end configured to fit the sternal notch or xiphoid process.

9. The system of claim 8 further comprising a linear extension connected to the elongated component on each side at one end and configured to be attached to the clavicle on the same side at the other end, and a wireless position sensor attached to the elongated component.

10. The system of claim 1 wherein the attachment member comprises a hard material.

11. The system of claim 1 wherein the attachment member comprises a disc.

12. The system of claim 1 wherein the protruding member comprises a clip.

13. The system of claim 12 wherein the protruding member is C-shaped.

14. The system of claim 1 wherein the wireless sensor comprises one of an optical marker and an infrared marker.

15. An attachment system comprising:
   a nipple attachment part having a curved opening through a thickness thereof, the curved opening sized to surround at least a portion of a breast nipple; and
   a protrusion coupled to the nipple attachment part, the protrusion constructed to receive one of a wired position sensor and a wireless position sensor.

16. The system of claim 15 further comprising a wired position sensor; and
   wherein the protrusion comprises a clip configured to retain the wired position sensor.

17. The system of claim 15 wherein the nipple attachment part comprises a disc.

18. The system of claim 15 wherein the nipple attachment part comprises an ultrasound transparent material.

19. The system of claim 15 wherein the nipple attachment part further comprises an orientation marker.

* * * * *

UNITED STATES PATENT AND TRADEMARK OFFICE
CERTIFICATE OF CORRECTION

PATENT NO. : 9,700,281 B2
APPLICATION NO. : 14/833419
DATED : July 11, 2017
INVENTOR(S) : Caluser Page 1 of 1

It is certified that error appears in the above-identified patent and that said Letters Patent is hereby corrected as shown below:

In the Specification

Column 2, Line 9, delete "rumor" and substitute therefore -- tumor --;

Column 2, Line 21, delete "users" and substitute therefore -- user's --; and

Column 2, Line 55, delete "tion is" and substitute therefore -- tion in --.

Column 5, Line 11, delete "sor used" and substitute therefore -- sors used --; and Column 5, Line 52, delete "shaped," and substitute therefore -- shaped --.

Column 7, Line 11, delete "angularly" and substitute therefore -- singularly --.

Column 8, Line 43, delete "patients" and substitute therefore -- patient's --.

Column 10, Line 15, delete "shin" and substitute therefore -- skin --;

Column 10, Line 48, delete "sensor" and substitute therefore -- sensor(s) --; and Column 10, Line 49, delete "(s) attached" and substitute therefore -- attached --.

Column 13, Line 22, delete "used tor" and substitute therefore -- used for --; and Column 13, Line 36, delete "these skilled" and substitute therefore -- those skilled --.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*